United States Patent
Obie

(10) Patent No.: US 10,451,533 B2
(45) Date of Patent: Oct. 22, 2019

(54) DEVICE FOR MEASURING DRYING, CURING, FILM FORMATION, AND RHEOLOGICAL PROPERTIES OF LIQUIDS AND FILMS

(71) Applicant: Wood Coatings Research Group, Inc., High Point, NC (US)

(72) Inventor: Ronald Obie, High Point, NC (US)

(73) Assignee: Wood Coatings Research Group, Inc., High Point, NC (US)

( * ) Notice: Subject to any disclaimer, the term of this patent is extended or adjusted under 35 U.S.C. 154(b) by 361 days.

(21) Appl. No.: 15/122,744

(22) PCT Filed: Mar. 12, 2015

(86) PCT No.: PCT/US2015/020281
§ 371 (c)(1),
(2) Date: Aug. 31, 2016

(87) PCT Pub. No.: WO2015/138797
PCT Pub. Date: Sep. 17, 2015

(65) Prior Publication Data
US 2017/0074767 A1    Mar. 16, 2017

Related U.S. Application Data

(60) Provisional application No. 61/952,904, filed on Mar. 14, 2014.

(51) Int. Cl.
*G01N 11/16*    (2006.01)

(52) U.S. Cl.
CPC ......... *G01N 11/162* (2013.01); *G01N 11/165* (2013.01); *G01N 2203/0092* (2013.01); *G01N 2203/0094* (2013.01)

(58) Field of Classification Search
CPC ............... G01N 11/162; G01N 11/165; G01N 2203/0092; G01N 2203/0094
USPC .................................. 73/54.26, 54.28, 54.38
See application file for complete search history.

(56) References Cited

U.S. PATENT DOCUMENTS 7,472,584 B2    1/2009    Seo et al.
7,607,098 B2    10/2009    Grehlinger et al.

FOREIGN PATENT DOCUMENTS

JP    2002202212 A    7/2002

OTHER PUBLICATIONS

International Search Report and Written Opinion issued in corresponding International Application No. PCT/US2015/020281, dated Aug. 14, 2015.

*Primary Examiner* — Daniel S Larkin
(74) *Attorney, Agent, or Firm* — Fox Rothschild LLP

(57) ABSTRACT

Provided is an apparatus and technique for monitoring the drying, cure, film formation, and viscoelastic properties of liquids, solidifiable liquid films, and the insitu measurement of viscoelastic properties of solidified films.

20 Claims, 8 Drawing Sheets

Side view of 60 mm diameter 150 micron deep well with coating and 25 mm diameter rim extended into liquid Top View Side View Side view of 60 mm diameter 150 micron deep well with coating and 25 mm diameter rim extended into liquid

DEVICE FOR MEASURING DRYING, CURING, FILM FORMATION, AND RHEOLOGICAL PROPERTIES OF LIQUIDS AND FILMS

CROSS-REFERENCE TO RELATED APPLICATIONS

This application is a U.S. national stage application under 35 U.S.C. § 371 of International Application No. PCT/US2015/020281, filed Mar. 12, 2015, which claims priority pursuant to 35 U.S.C. § 119 to U.S. Patent Application Ser. No. 61/952,904, filed Mar. 14, 2014, each of which is hereby incorporated by reference in its entirety.

BACKGROUND OF THE INVENTION

Field of the Invention

The present invention is targeted towards an apparatus and technique for monitoring the drying, cure, film formation, and viscoelastic properties of liquids, solidifiable liquid films, and the insitu measurement of viscoelastic properties of solidified films.

The application, appearance, and performance of liquids and films, particularly coatings and adhesives, depend to a great extent on such properties as viscosity, drying rate or carrier evaporation, rate of cure or crosslinking, film consolidation, and viscoelastic characteristics of the film during film formation and of the final film itself. For example, to develop the most advantageous coating and/or adhesive, these properties need to be monitored and adjusted according to the situation at hand.

For instance, one may need to adjust the amount of retarder solvent in a coating to improve the length of time the film remains mobile for improved flow, leveling, and/or penetration; or one may need to incorporate pigments or minerals into the system to improve hardness development for example; further, one may need to measure the effect of certain coalescent agents on film formation and final coating moduli; one may need to evaluate the impact of catalyst type and concentration on cure rate and viscoelastic properties; further, rheological control additives may be required to improve application and appearance. It is of critical importance to control these properties for best performance, and in order to control these properties, they must first be accurately measured.

The viscosity of liquids are measured a number of ways; for instance, ASTM (American Society for Testing and Materials) D1200 describes viscosity measurement by time of liquid effluent from a Ford Viscosity Cup; ASTM D5478 describes the viscosity measurement of materials by a Falling Needle Viscometer; ASTM D 4287 describes the high shear viscosity measurement using a cone and plate viscometer; ASTM D1545 describes viscosity measurement of transparent liquids using a bubble time method. The above are examples of viscosity measurement methods; all however, typically only result in viscosity of the liquid before application of such liquid to a substrate, and hence provide no analytical means of accessing the viscosity of the material on the substrate, or on its drying behavior once applied, or on the final consolidated film viscoelastic properties.

The drying properties of a liquid coating film have traditionally been determined by a variety of methodologies. For instance, it is common to measure the dry-to-touch of a drying film; in this method, the surface of the film is periodically touched with the analyst finger and is a subjective assessment of coating dry.

ASTM D5895 provides a method of evaluation of coating dry by first applying a coating to a substrate such as glass, and then placing a stylus into the coating; the stylus is then moved in either a circular or linear motion at constant speed; coating dry is assessed by monitoring the resulting track of the stylus in the liquid coating and in the consolidated film, e.g., set-to-touch, tack-free, dry-hard, and through-dry times are determined qualitatively by the analyst.

Drying may be evaluated by gravimetric means where the film is monitored for change in weight as a function of time. This method allows assessment of solvent evaporation, but provides no assessment of crosslinking reactions.

Coating film properties may be assessed by evaluation of the film after most of the solvent has evaporated from the film; these methods include measurement of hardness development as a function of time such as pencil hardness, scratch hardness, tukon hardness, etc. These methods yield limited insight into the film formation consolidation process and essentially no insight into the behavior of the film while in its liquid state.

ASTM D4473 provides a method of assessing cure rate as measured by time to dynamic gel point displayed by complex viscosity measurements at 100 pa·s using a plate-plate configuration. This method is most useful for liquids that do not contain volatile solvents, as the presence of volatile solvents may unduly impact true film consolidation, crosslinking, and final viscoelastic behavior measured.

A drawback of the methods described above for assessing dry and cure is that many are quite subjective and others provide only a snapshot the film consolidation process, or further, do not allow evaporation of volatiles from the film resulting in erroneous drying behavior results. Further, liquid as well as consolidated films display viscoelastic behavior; measurement of viscoelastic behavior during film drying and after film consolidation provides a more accurate and detailed analysis of the drying process and physical properties of the consolidated film.

U.S. Pat. Nos. 7,185,530 B2, and 7,472,584 B2 by Seo et al. describe an apparatus and method for monitoring the viscoelastic properties of a liquid film. In this invention, the authors describe an apparatus which includes a substrate for supporting a liquid film and a partially submerged T-bar probe attached to a conventional rheometer. The apparatus is said to be particularly useful for comparing the impact of various components on drying rate, particularly at the early stage of film formation. In fact, it is stated in both U.S. Pat. No. 7,185,530 B2 and U.S. Pat. No. 7,472,584 B2 that tests utilizing this T-bar type probe should be ceased before the viscosity becomes too high to avoid damaging the probe.

Further, oscillatory frequency sweep tests utilized to measure film drying appear to be conducted at high strain rates (100%) and high frequency rates (up to 25 rad/sec); these high rates are required to improve measurement sensitivity; however, at these strain rates, one may be changing the structural properties of the sample under test (Thomas G. Mezger, The Rheology Handbook, $2^{nd}$ Edition, copyright 2006, Vincent Network GmbH & Co, KG, Hannover) thusly resulting in "arbitrary" measurement data being reported. Further, rheologically, the greatest stress on the T-bar probe is expected to exist at the opposite ends of the probe. This can easily result in flexural distortion of the probe during the test, resulting in possible inaccuracies in the reported data. U.S. Pat. No. 7,472,584 B2 describes the use of reinforcing bars to the T-bar probe. Although this reinforcement is expected to mitigate to a certain degree the weaknesses of U.S. Pat. No. 7,185,530 B2, deflection of the small radius bar is still possible, and becomes more problematical for higher modulus coatings. The more the material cures, the greater the potential deflection of the bar and hence the greater the potential error of the measurement. Further, this deflection tendency limits utility of the bar to measurement of final consolidated film properties with the device as described in 7185530 B2 or 7472584 B2.

BRIEF SUMMARY OF EMBODIMENTS OF THE INVENTION

Given the aforementioned deficiencies, a need exists for a means of analytically and reproducibly measuring the drying, solidification, cure, and final viscoelastic properties of a liquid film on a substrate.

Certain circumstances, embodiments of the invention provide an apparatus for analytically examining the drying, curing, and solidification properties of a coating, adhesive, or liquid film. The embodiment provides minimal intrusion into a film while allowing relatively free and/or controlled evaporation of volatiles that might be present or generated in the film during drying or curing.

In this way, the apparatus closely mimics an actual drying, solidification, and/or curing process. The embodiment allows objective measuring change in viscosity and elasticity of the film as a function of time, as well as allows insitu viscoelastic/dynamic mechanical measurement of final film properties as a function of temperature. The article of the present invention comprises a substrate, such as a well, trough, or plate, a rim probe mounted so as to contact a liquid film on the substrate, a means of effecting relative movement of the probe contacting the film (such as a rheometer) to obtain a measurement of the drying, curing, and solidification properties of the film as a function of time.

In another embodiment, a process is provided for analytically quantifying the viscoelastic properties of a liquid applied to a substrate comprising the steps of contacting the rim probe with the liquid, moving the face of the probe parallel to the substrate while in contact with the liquid film while the film is drying, curing, or solidifying, and monitoring the change in the drying, curing, and solidification properties of the film.

In yet another embodiment, a process is provided for measuring the viscoelastic properties of a consolidated film on a substrate insitu comprising the steps of contacting a probe with the liquid film, allowing the liquid film to solidify while the probe is in contact with the film, applying an oscillatory force to the probe and hence to the consolidated film, and measuring the resultant response from the applied force as a function of temperature.

Various embodiments of the invention are described below. Any of the embodiments of the invention may be used alone, or may be taken in various combinations. Some of the combinations according to the invention may be used to formulate coating compositions having unexpected properties in view of the state of the art, and are intended to be encompassed within the scope of the invention. Additional objects and advantages of the invention are discussed in the detailed description that follows, and will be obvious from that description, or may be learned by practice of the invention. It is to be understood that both this summary and the following detailed description are exemplary and explanatory only, and are not intended to restrict the scope of the invention.

BRIEF DESCRIPTION OF THE DRAWINGS

The accompanying figures, which are incorporated herein and form a part of the specification, illustrate the present invention and, together with the description, further serve to explain the principles of the invention and to enable a person skilled in the pertinent art to make and use the invention.

DETAILED DESCRIPTION OF THE EMBODIMENTS

Figure 1:
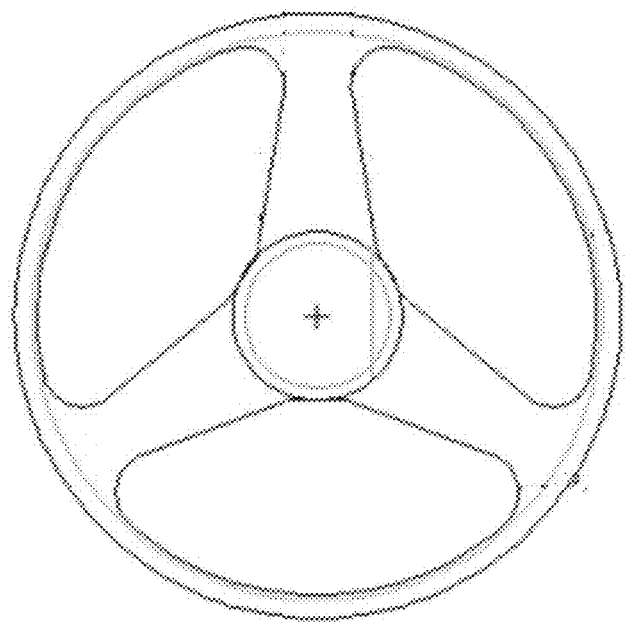
FIG. 1 illustrates a 25 mm rim probe used in FIGS. 4-8 in top view and from a side view. The reinforcing spokes are recessed away from the measurement rim and are not exposed to the liquid. In this example, a tool steel sleeve is used to cover a stainless steel shank in order to adjust the size of the shank to 6.99 mm.
Figure 1:
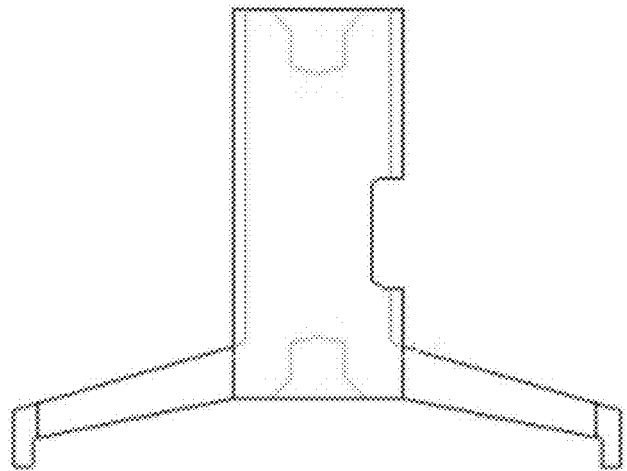

As mentioned above, embodiments of the present invention may be more readily understood by referring to the following detailed examples and the aforementioned drawings and figures. It is to be understood that the present invention is not limited to the specific apparatus, processes, procedures, and/or process conditions for measuring the drying, curing, viscoelastic, and solidification properties of liquids as mentioned here as these properties may vary for specific liquids and require certain specific apparatus and processes and/or process conditions for measurement.

In the specification and claims, the singular forms "a," "an," and "the" include plural referents unless the context clearly dictates otherwise.

Ranges are expressed herein as from "about" or "approximately" another particular value. Ranges expressed as such include a separate embodiment of the ranges.

The terms "containing," or "including." means that as a minimum the named apparatus, component, or procedure etc. must be present in the article or method. This does not preclude the presence of other materials, article, elements, or procedures even if they are not specifically identified.

Viscosity refers to the resistance of a liquid to flow.

Rheology is the science of deformation and flow of matter.

Viscoelastic refers to the behavior of all real materials displaying both viscous and elastic behavior. Viscous behavior is the liquid-like behavior of a material, while elasticity is the solid-like behavior of the material. Such values can be expressed for both liquid materials as well as solid materials. With respect to study of drying and curing, these values are expressed as a function of time.

Complex viscosity refers to a frequency-dependent viscosity function determined during forced harmonic oscillation of shear stress.

Storage modulus refers to the solid-like behavior of a liquid or solid material.

Loss modulus refers to the viscous response of a liquid or solid material

Rheometry is the quantifying technology used to ascertain rheological data by use of a Rheometer. Thus a rheometer may be used to measure such rheological properties as viscosity, modulus, elasticity, normal force, frequency dependence, strain amplitude dependence, dynamic mechanical properties, and others. Both liquids and solids may be investigated using a rheometer which moves a measuring system, or probe, in a rotational or dynamic oscillatory motion relative to a substrate by means of a motor, and sensing the response or resistance of the test material by means of a detector, sensor, or transducer.

One embodiment of the invention includes the discovery of an improved, method to monitor changes in the viscoelastic properties of liquid films such as coatings and adhesives during the drying or curing process. Particularly advantageous benefits of the discovery include excellent sensitivity of the rim probe as opposed to a bar probe due to improved surface contact area, e.g. the entire rim detects the sample, minimal requirement for disturbance or disruption of the liquid or film by use of exceptionally low strain and frequency allowing data to be measured in the linear viscoelastic region, exceptionally low tendency for torsional bending of probe to impact data, the ability to thoroughly characterize the rim probe from a rheological standpoint and hence calculate sample rheological parameters from the sensed data, the ability to measure low viscosity as well as high viscosity materials, the ability to measure weak as well as high modulus materials without damaging the probe or having to remove the probe before complete solidification of the film. Other particularly advantageous benefits of the invention include the ability to measure insitu, dynamic mechanical properties of not only liquids, but of completely consolidated and cured films, e.g., dynamic mechanical thermal analysis, frequency sweeps, amplitude sweeps, etc. without removing the probe or without additional sample preparation.

Another embodiment of the present invention is directed to an apparatus for measuring the viscoelastic and curing properties of a liquid film. The apparatus comprises a substrate, such as a well, channel, or plate, and a probe, such as a thin hard rim, preferably mounted on a rheometer as defined above.

Through use of an input signal and detection system as by use of a rheometer, the probe detects the viscoelastic response of the liquid film over time as the liquid film cures or solidifies. The torque and the phase angle along with the geometrical characteristics of the rim probe are used to determine the complex viscosity (eta*), the loss modulus (G") and the storage modulus (G') of the drying or curing film as a function of time.

In a preferred embodiment, the probe is contacted with the liquid film immediately after the liquid film is introduced into the well. Through use of dynamic normal force control or some other mechanism, the probe can be made to remain in contact with the liquid film throughout the drying, curing, consolidation, or aging process.

Another embodiment of the present invention is directed to an apparatus for determining dynamic mechanical properties such as dynamic mechanical thermal analysis, frequency sweeps, amplitude sweeps, etc. of solidified and cured films, insitu. In a dynamic mechanical thermal analysis (DMTA), the physical and thermodynamical properties of a solidified sample are measured as a function of the temperature.

The deformation load is kept low to avoid destroying or changing the structure of the material. Frequency sweeps are tests run in the oscillatory mode whereby the response of the test material is monitored as a function of variable frequency while keeping the amplitude and temperature constant. Frequency sweeps are used to investigate time dependent shear behavior.

Amplitude sweeps are tests run in the oscillatory mode whereby the response of the test material is monitored as a function of variable amplitude while keeping the frequency and temperature constant. Amplitude sweeps can be used to investigate the structural character of a sample and to identify the linear viscoelastic (LVE) range of a material.

After solidification of the film, while the probe is in contact with the completely dried/cured film viscoelastic response of the film is monitored as a function of temperature, frequency, or amplitude, etc. The torque and the phase angle are used to determine the loss modulus (G") and the storage modulus (G'), and the ratio of these, tan delta, as a function of temperature. In a preferred embodiment, the probe remains in contact with the solidified liquid film after a drying experiment, and DMTA, frequency sweep, or amplitude sweep, subsequently performed.

The invention is suitable for determining the viscoelastic properties, the solidifying properties of a large variety of different types of liquid films, and the subsequent dynamical thermal properties of the subsequently consolidated films. The types of liquid films which are readily analyzed and studied by the invention include, but are not limited to thermoplastic, thermoset, solvent based, water based, and solvent free films.

For example, the embodiments are suitable for monitoring films which solidify as a consequence of crosslinking, such as 2K epoxies, 2K polyurethanes, ultraviolet and electron beam cured films, peroxide cured films, oxidizable films, free-radically cured films, phenolic cured films, urea-formaldehyde and melamine formaldehyde cured films, etc. Further films that dry by solvent or water evaporation may also be monitored. The embodiments are also useful for monitoring the cure and dry of adhesives.

The embodiments are useful for monitoring the dry of pigmented compositions such as inks and coatings. Other examples of the many applications of the invention include drying of paints, water flash off of aqueous UV coatings, curing of UV coatings, drying and hardening of adhesives, etc. Further, the invention allows the assessment of the influence of undercoats and/or substrate on the dry of a subsequent coating, for example. Further, once the film is consolidated (e.g., cured), the invention enables the dynamical mechanical analysis of the consolidated film to be assessed, insitu.

The film thickness of the sample to be assessed may be varied by the depth of the well. It is preferable that the depth, size, shape, or configuration of the well mimic an actual liquid film drying or curing process. It is also preferable that the temperature profile and air flow rate to which the film would be exposed in an actual liquid solidification process be reproduced as well. For example, if a coating or paint is the liquid film to be monitored, then the well is preferably shallow having a depth ranging from about 5 microns to about 10000 microns, preferably from about 10 microns to about 1000 microns, more preferably from about 25 microns to about 300 microns, and most preferably from about 100 microns to about 200 microns.

In order to avoid edge drying effects, the ratio of the diameter or width of the well to that of the rim probe should be great enough to avoid the effects of premature edge drying effects. In one embodiment, the ratio of the diameter or width (depending on whether the well is square, rectangular, circular, or other shape) of the well to that of the rim probe ranges from about 1.1 to about 20, preferably about 1.2 to about 12.5, and more preferably from about 1.3 to about 2.5.

Figure 2:
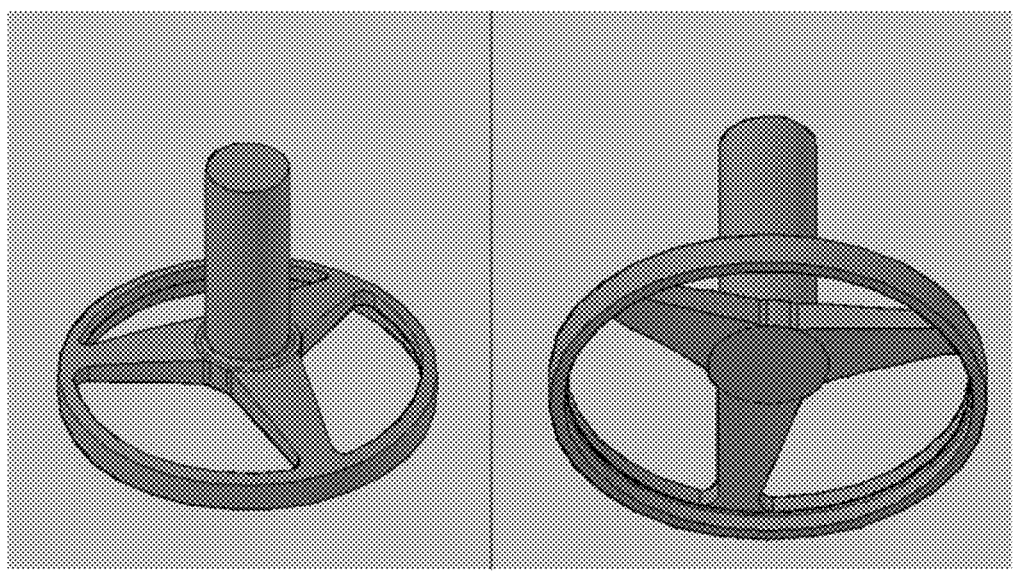
FIG. 2. Illustrates a 25 mm rim probe in 3-D.

The circular rim probe of the embodiments (FIGS. 1 and 2) includes a circular rim that is contacted or submerged in the liquid film to be tested and a means of attaching the circular rim to the rheometer. In one aspect of the invention, the rim is set off from another circular rim which is attached to reinforcing spokes that are then attached to a vertical shank for effecting attachment to the rheometer. A variety of spoke structures, configurations, and shapes may be utilized to attach the rim to the rheometer, such as bars, rods, rectangles, shafts, etc.

The shank may have a collar type structure which assists with placement of rim probe when attaching to the rheometer. Only the portion of the rim that is not attached to the reinforcing spokes make contact with the liquid material. The spokes are spaced with air gaps between them so that evaporation of volatiles is not impeded. The probe has sufficient surface area contacting the liquid film so that it can detect the resistance to the imposed stress, but small enough so that the probe does not interfere with the solidification process. Further, the probe has sufficient surface area such that it is sensitive to the resistance of the film without imposing a large strain.

For paint and coating applications, a preferred rim has an outer diameter in the range from about 2 mm to about 80 mm, preferably about 5 mm to about 50 mm, and more preferably from about 8 mm to about 40 mm. A preferred rim has an inner diameter in the range from about 0.5 mm to about 78.5 mm, preferably about 3.5 mm to about 48.5 mm, and more preferably from about 6.5 mm to about 38.5 mm.

Clearance under spokes at the rim can range from about 0.1 mm to about 5 mm, preferably about 0.5 mm to 3 mm, more preferably, about 0.8 mm to 2 mm. The area of the bottom face of the contact area of the rim can range from about 5 mm$^2$ to about 200 mm$^2$ preferably about 120 mm$^2$ to about 200 mm$^2$, more preferably, about 40 mm$^2$ to about 120 mm$^2$. The cross-sectional face of the rim is not limited to a rectangular shape as it may be circular, rounded or v-shaped in nature.

However, the rectangular cross-section may allow more specific calculation of probe rheological characteristics. The rigidity of the rim (without being brittle) should be such that it is not affected by the dynamic properties of the liquid film as it solidifies, and if desired the dynamic properties of the consolidated film for which Dynamic mechanical analysis (e.g., DMTA, Frequency and Amplitude Sweeps) measurements are performed. Suitable material examples include ultrahigh strength steel alloys, stainless steel, high carbon steel, and tungsten carbide and the like. While these dimensions are provided for the present invention, specifically the use of a rheometer and the monitoring of solidification properties of paints and other coatings, and dynamic mechanical analysis of consolidated films and coatings, it is within the scope of the present invention to modify the rim probe dimensions to suit the film and/or coating to be tested.

The drying and curing of a liquid film is dependent upon the thickness of the liquid film. In a preferred embodiment of the invention, the thickness of the film is uniform in the portion of the film being analyzed. Therefore the thickness of the film is controlled. This may be accomplished by varying the depth of the well, or varying the deposition rate of the test liquid, either by metering a precise volume or weight per area. The test liquid may be deposited by a variety of means such as by casting, pipetting, pouring, flowing, or injecting, rolling, spraying, etc. When the liquid that is to be studied is poured or metered into the well, for example, the top surface of the well is leveled to provide a consistent film thickness.

The film may be leveled by drawing a flat edge such as a glass slide or a grind gage scraper across the raised flat surface of the well. In another embodiment, a precise amount of material may be applied to a well or trough of known dimensions and allowed to level. In still another embodiment, a precise amount of liquid film may be metered onto a flat plate by using a film casting knife designed for a specific film thickness. In yet another embodiment, a specific amount of coating may be applied by spray or roll application gravimetrically to a substrate and subsequently measured. After application of the liquid film to a substrate, a probe is then contacted with the liquid film.

In a preferred embodiment, the rim of the probe is submerged into the liquid film to a point where it does not contact the substrate, and where the clearance of the rim under the spokes is not reached or exceeded. The gap between the bottom of the well (substrate) and the bottom portion of the rim probe will depend on the characteristics of the liquid and subsequent film to be studied, as well as the type and size of the probe and the depth of the liquid film being analyzed, the shape of the well, and the clearance under the spokes at the rim of the probe. The typical gap between the substrate and the bottom of the rim is in the range of about 10 microns to about 200 microns, depending upon on the clearance of the rim under the spokes, the depth of the well and the liquid film thickness.

The curing and drying rate of liquid films, particularly coatings and adhesives are normally sensitive to film thickness, humidity, temperature and air flow rate. Equally, dynamic mechanical performance properties of consolidated materials are also sensitive to environmental conditions. Therefore, at the very least, these parameters should be monitored or controlled. In a preferred embodiment a controlled environment (such as use of an environmental chamber) is utilized to provide constant humidity, temperature and gas flow rate to the liquid film and consolidated film.

The rim probe may be mounted by any appropriate means. In a preferred embodiment, the probe is mounted on a rheometer capable of moving the probe or sample relative to each other under controlled stress and/or strain and measuring the resistance and phase of such movement. The probe may be moved in any manner that will provide resistance that can be measured. In a preferred embodiment, the rim probe is moved in an oscillatory manner and the response of the liquid or consolidated film to such oscillatory movement is measured. In a preferred embodiment, the rim probe response to an imposed oscillatory movement is monitored as a function of time as the liquid dries. Any means may be used to accomplish movement such as a motor or other mechanical means. The response detected by the probe can be measured by any suitable method such as a transducer or other sensor. From the response and phase angle, complex viscosity, loss modulus, and storage modulus as well as other rheological properties of the liquid film can be determined as a function of time.

Figure 3:
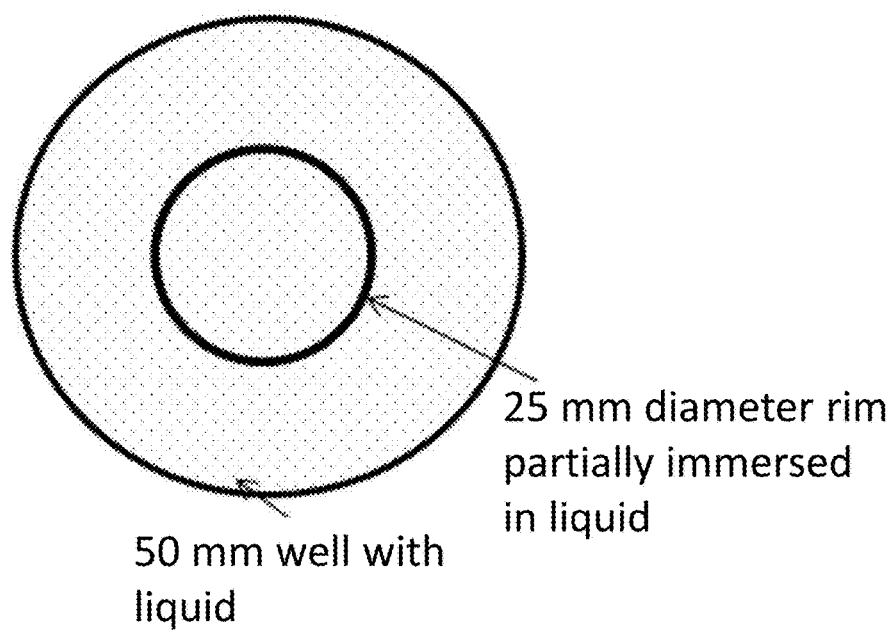
FIG. 3. Illustrates a top view of a 25 mm diameter rim partially immersed in a liquid contained in a 60 mm diameter well of 150 micron depth.
Figure 4:
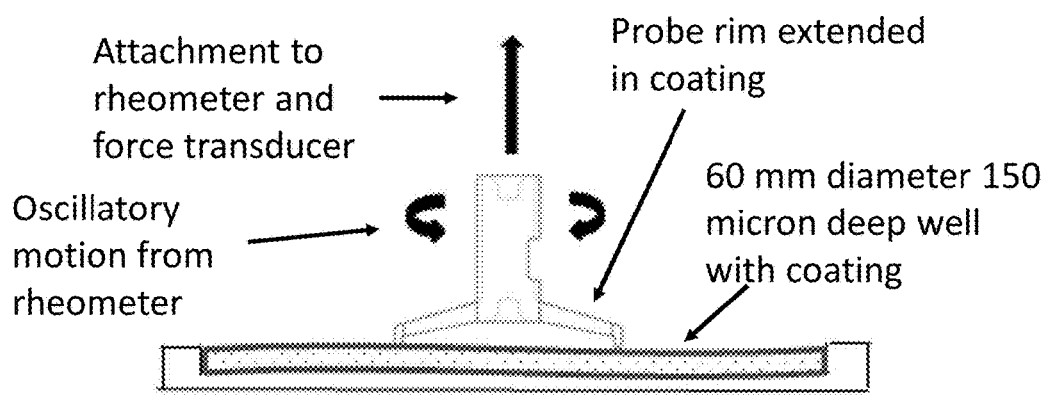
FIG. 4. Illustrates a side view of a 25 mm diameter rim probe partially immersed in a liquid film contained in a 60 mm diameter 150 micron deep well. The probe shank is attached to a motor capable of oscillatory motion, and capable of measuring the torque response and damping of the imposed stress.

Referring to FIG. 3, the solidification properties of a solidifiable liquid may be measured using such an apparatus as displayed in the diagram, which comprises a rim mounted to a sensor and/or rheometer which measures the rheological properties of the liquid film. The liquid film is supported by a substrate having a well. The shape and dimensions of the well can vary and are not limited to a circular shape. A rim functioning as a probe is mounted to the rheometer and is partially submerged in the liquid film. The rim may penetrate the liquid film so long as the rim does not contact the substrate. A motor provides movement between the rim and the substrate and a sensor measures the resistance to the movement of the rim probe to the liquid film as the film dries or cures. The position of the probe in the liquid film may be adjusted by changing the position of the sensor head to which the probe is connected.

The following examples are illustrative, but not limiting, of the methods of the present invention. Other suitable modifications and adaptations of the variety of conditions and parameters normally encountered in the field, and which are obvious to those skilled in the art, are within the spirit and scope of the invention.

All patents and publications cited herein are fully incorporated by reference herein in their entirety.

EXAMPLES

In the following examples, the drying rate and rheological properties were measured in a closed chamber at a temperature between 24-26 degrees Celsius

Example 1

A 150 micron deep, 60 mm diameter circular well was filled with approximately 0.5 mL of a nitrocellulose coating formulation having a vehicle analysis of approximately 40% RS ½ second nitrocellulose, 24% short oil coconut alkyd (Aroplaz 2575X60 available from Reichhold, Research Triangle Park, N.C.), 16% maleic modified hard resin (Unirez 7204 available from Union Camp Chemical Corporation, Jacksonville, Fla.), and 20% phthalate plasticizer (Di isononyl phthalate (DINP)) using a disposable syringe. The free solvent composition was composed by volume of 36.19% butyl acetate, 7.54% butanol, 5.80% Dowanol PM, and 50.47% Xylene. The coating formulation contained 0.5% on total weight silica gel matting agent (Silysia 350 from Fuji Silysia Chemical, Durham, N.C.).

In example 1, the well was immediately scraped with the edge of a grind gage scraper from Precision Gage and Tool, 375 Gargrave Road, Dayton, Ohio 45449, to uniform the surface and the time of scrape down was noted. A rim probe of dimensions OD 24.99 mm. ID 23.49 mm having an area of the bottom face of 57.1141 mm$^2$ was lowered to a 0.100 mm gap, and then the dynamic mechanical analyzer (MCR 301 available from Anton Paar Ashland Va.) was run at 0.1% strain and 10 s$^{-1}$ frequency.

Figure 5:
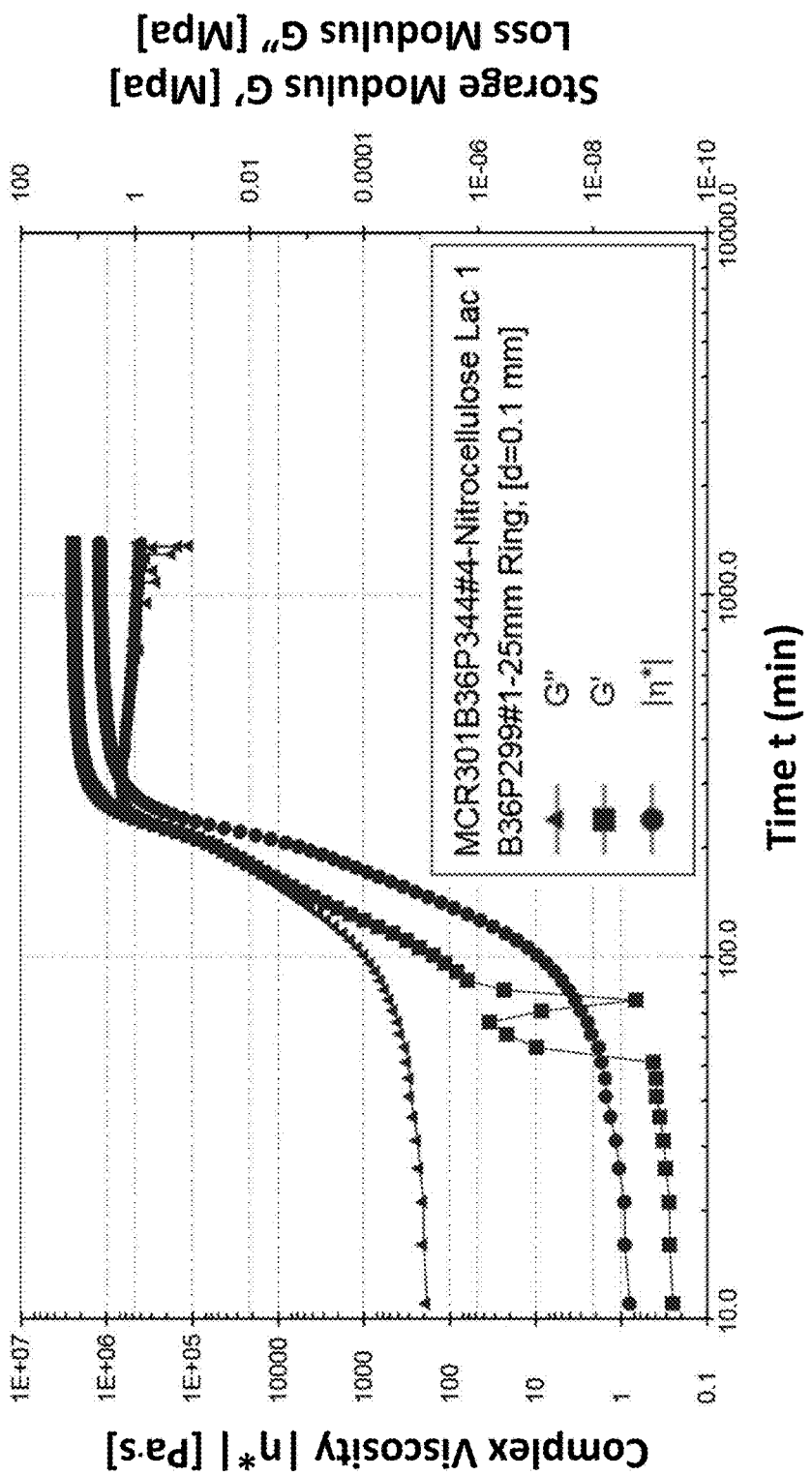
FIG. 5. Illustrates a graphic representation of the viscoelastic properties, (complex viscosity, loss and storage moduli) of a nitrocellulose lacquer in a 150 micron well as a function of time.

Changes in viscoelastic properties, complex viscosity (eta*), storage modulus (G'), and loss modulus (G") with time are illustrated in FIG. 5. Due to the sensitivity of the rheometer and the advantageous configuration of the invention, small torques are easily sensed, even during the early stages of the drying.

Further, it is advantageous to be able to monitor the sample at extremely low strain rates and low frequency as this minimizes changing the internal structure of the sample and more realistically mimics true sample drying without disturbance of the liquid film by the probe. This is in contrast to the T-bar probe described in U.S. Pat. Nos. 7,185,530 B2, and 7,472,584 B2 by Seo et al. which apparently requires a strain of 100% and a frequency of 25 rad/sec.

Further, in contrast to the T-bar probe described by Seo, there is no need to remove the probe before complete consolidation of the film due to fear of damage to the probe. As illustrated in FIG. 5, the viscoelastic properties of the film are followed completely to full film consolidation, e.g. to an approximate constant storage modulus and complex viscosity. The consolidated film may then be evaluated by dynamic mechanical analysis (DTMA, Frequency sweep, Amplitude sweep and others) insitu without further preparation.

Further, the probe is easily cleaned and prepared for the next run by sonication in a cleaning solution consisting of approximately 35% N-Methyl-2-Pyrrolidone, approximately 35% ethylene glycol monobutyl ether, approximately 15% xylene, and approximately 15% Methyl ethyl ketone. Water may be added to the solution. The cleaning solution is effective at cleaning the probe even if the liquid is a thermoset composition.

Example 2

A 150 micron deep, 60 mm diameter circular well was filled with approximately 0.5 mL of an aqueous lacquer composed of Rhoplex CL-204 polymer from Dow Coating Solutions, Midland Mich. The polymer was coalesced with 35% ethylene glycol monobutyl ether on solid polymer. The coating contained 0.33% RM825 rheology control additive from Dow Coating solutions, and 0.73% BYK 346 flow and leveling additive from BYK USA, Wallingford, Conn. The coating solution was developed to 25% volume solids with water and added to the well using a disposable syringe.

In example 2, the well was immediately scraped with the edge of a grind gage scraper from Precision Gage and Tool, 375 Gargrave Road, Dayton, Ohio 45449, to uniform the surface and the time of scrape down was noted. A rim probe of dimensions OD 24.99 mm, ID 23.49 mm having an area of the bottom face of 57.1141 mm$^2$ was lowered to a 0.100 mm gap, and then the dynamic mechanical analyzer (MCR 301 available from Anton Paar Ashland Va.) was run at 0.1% strain and 10 s$^{-1}$ frequency. Changes in viscoelastic properties, complex viscosity (eta*), storage modulus (G'), and loss modulus (G") with time are illustrated in FIG. 6.

Due to the sensitivity of the rheometer and the advantageous configuration of the invention, small torques are easily sensed, even during the early stages of the drying. Further, it is advantageous to be able to monitor the sample at extremely low strain rates and low frequency as this minimizes changing the internal structure of the sample and more realistically mimics true sample drying without disturbance of the film by the probe. This is in contrast to the T-bar probe described in U.S. Pat. Nos. 7,185,530 B2, and 7,472,584 B2 by Seo et al. which apparently requires a strain of 100% and a frequency of 25 rad/sec. Further, in contrast to the T-bar probe described by Seo, there is no need to remove the probe before complete consolidation of the film due to fear of damage to the probe.

Figure 6:
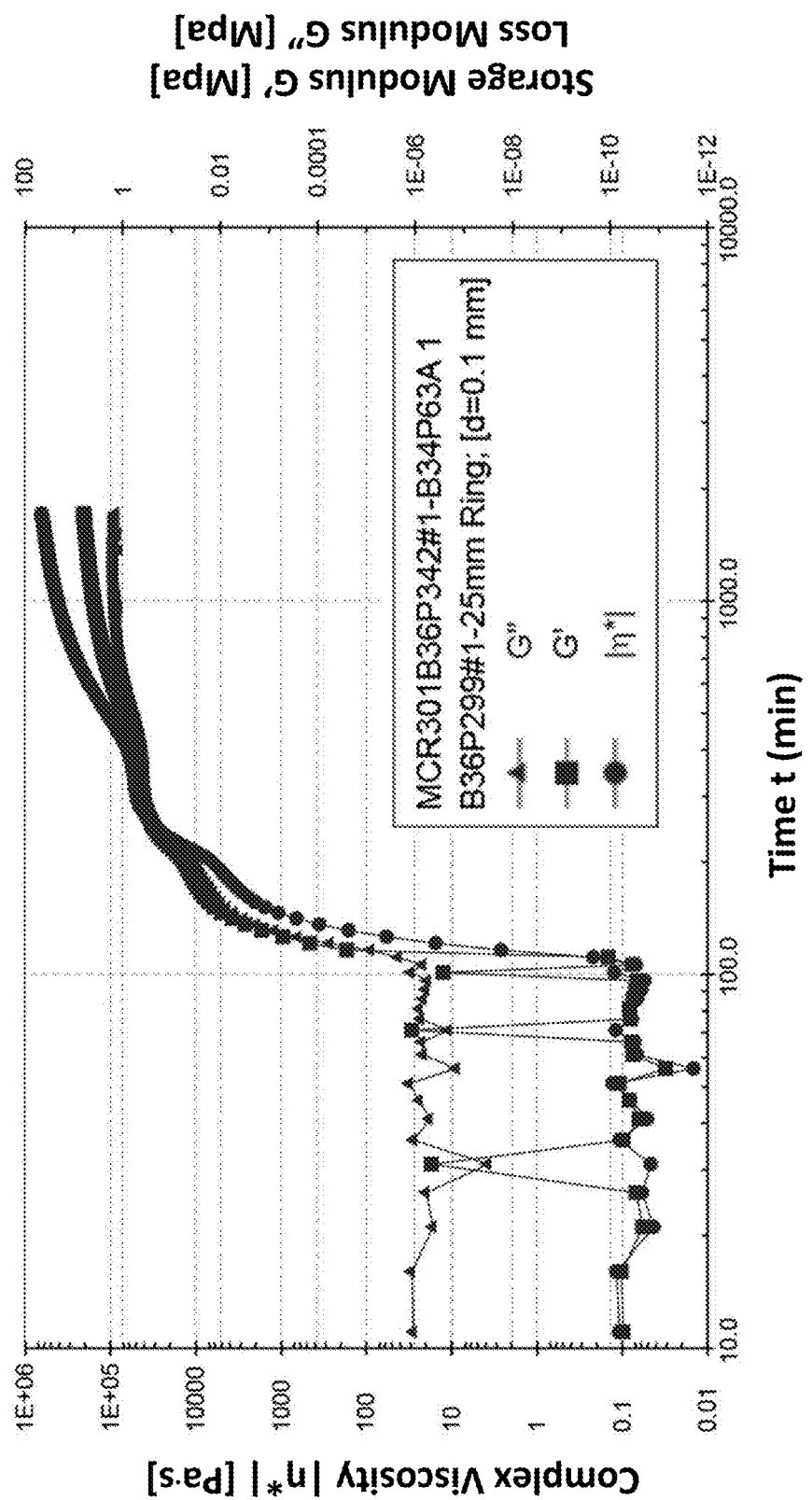
FIG. 6. Illustrates a graphic representation of the viscoelastic properties, (complex viscosity, loss and storage moduli) of an aqueous acrylic lacquer that utilizes ethylene glycol monobutyl ether as coalescing additive in a 150 micron well as a function of time.

As illustrated in FIG. 6, the viscoelastic properties of the film are followed completely to full film consolidation, e.g. to an approximate constant storage modulus and complex viscosity. The consolidated film may then be evaluated by dynamic mechanical analysis (DTMA, Frequency sweep, Amplitude sweep and others) insitu without further preparation.

Further, the probe is easily cleaned and prepared for the next run by sonication in a cleaning solution consisting of approximately 35% N-Methyl-2-Pyrrolidone, approximately 35% ethylene glycol monobutyl ether, approximately 15% xylene, and approximately 15% Methyl ethyl ketone. Water may be added to the solution. The cleaning solution is effective at cleaning the probe even if the liquid is a thermoset composition.

Example 3

A 150 micron deep, 60 mm diameter circular well was filled with approximately 0.5 mL of an aqueous lacquer composed of Rhoplex CL-204 polymer from Dow Coating Solutions, Midland Mich. The polymer was coalesced with 35% Propylene glycol butyl ether (Dowanol PnB from the Dow Chemical Company) on solid polymer. The coating contained 0.33% RM825 rheology control additive from Dow Coating solutions, and 0.73% BYK 346 flow and leveling additive from BYK USA. Wallingford, Conn. The coating solution was developed to 25% volume solids with water and added to the well using a disposable syringe.

Figure 7:
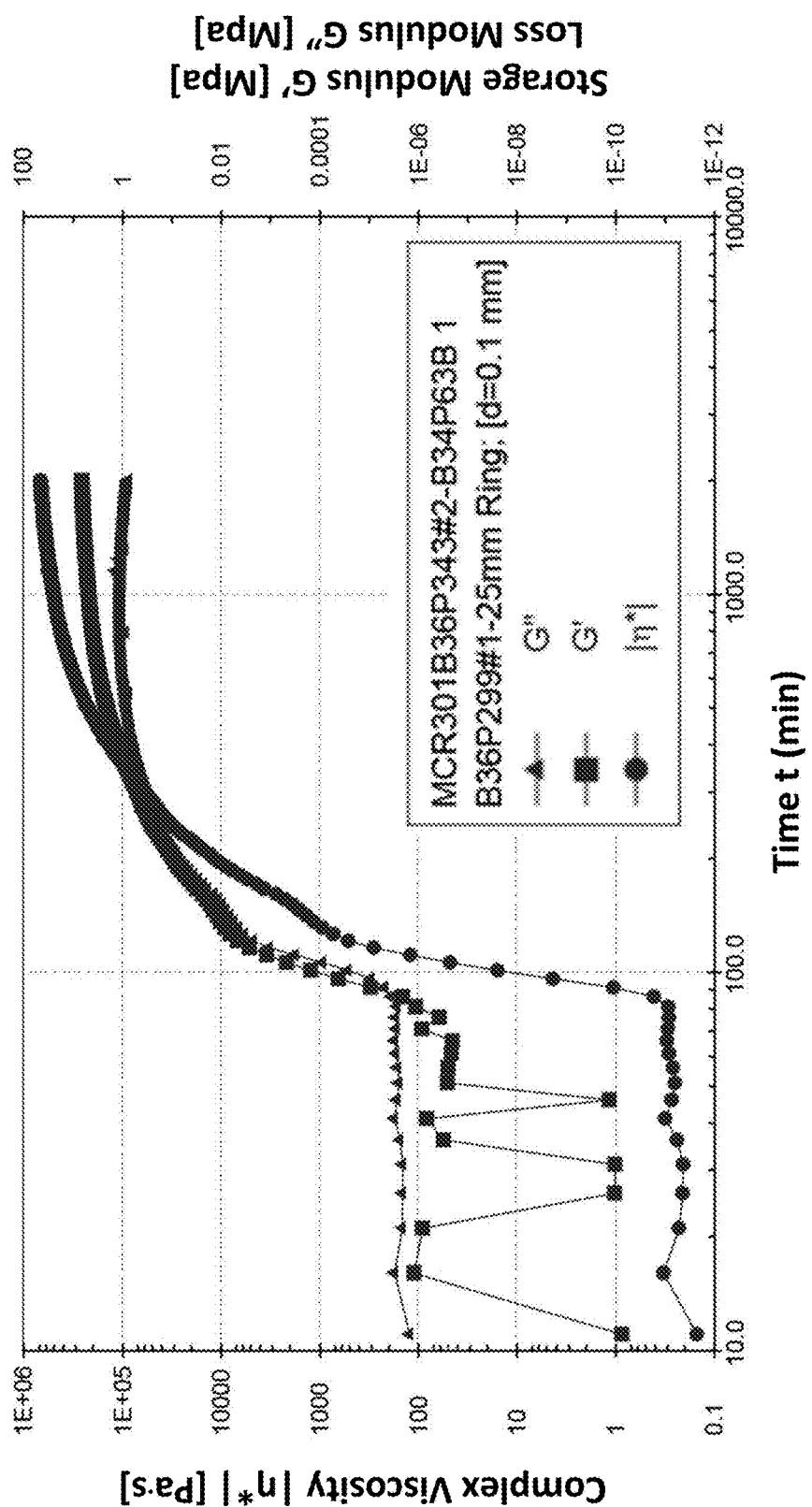
FIG. 7. Illustrates a graphic representation of the viscoelastic properties, (complex viscosity, loss and storage moduli) of an aqueous acrylic lacquer that utilizes propylene glycol butyl ether as coalescing additive in a 150 micron well as a function of time.

In example 3, the well was immediately scraped with the edge of a grind gage scraper from Precision Gage and Tool, 375 Gargrave Road, Dayton, Ohio 45449, to uniform the surface and the time of scrape down was noted. A rim probe of dimensions OD 24.99 mm, ID 23.49 mm having an area of the bottom face of 57.1141 mm$^2$ was lowered to a 0.100 mm gap, and then the dynamic mechanical analyzer (MCR 301 available from Anton Paar Ashland Va.) was run at 0.1% strain and 10 s$^{-1}$ frequency. Changes in viscoelastic properties, complex viscosity (eta*), storage modulus (G'), and loss modulus (G") with time are illustrated in FIG. 7.

Due to the sensitivity of the rheometer and the advantageous configuration of the invention, small torques are easily sensed, even during the early stages of the drying. Further, it is advantageous to be able to monitor the sample at extremely low strain rates and low frequency as this minimizes changing the internal structure of the sample and more realistically mimics true sample drying without disturbance of the film by the probe. This is in contrast to the T-bar probe described in U.S. Pat. Nos. 7,185,530 B2, and 7,472,584 B2 by Seo et al. which apparently requires a strain of 100% and a frequency of 25 rad/sec.

Further, in contrast to the T-bar probe described by Seo, there is no need to remove the probe before complete consolidation of the film due to fear of damage to the probe. As illustrated in FIG. 7, the viscoelastic properties of the film are followed completely to full film consolidation, e.g. to an approximate constant storage modulus and complex viscosity. The consolidated film may then be evaluated by dynamic mechanical analysis (DTMA, Frequency sweep, Amplitude sweep and others) insitu without further preparation.

Further, the probe is easily cleaned and prepared for the next run by sonication in a cleaning solution consisting of approximately 35% N-Methyl-2-Pyrrolidone, approximately 35% ethylene glycol monobutyl ether, approximately 15% xylene, and approximately 15% Methyl ethyl ketone. Water may be added to the solution. The cleaning solution is effective at cleaning the probe even if the liquid is a thermoset composition.

Example 4

A 150 micron deep, 60 mm diameter circular well was filled with approximately 0.5 mL of an aqueous lacquer composed of Rhoplex CL-204 polymer from Dow Coating Solutions, Midland Mich. The polymer was coalesced with 35% Exxate 700, formerly from Exxon Chemical Company on solid polymer. The coating contained 0.33% RM825 rheology control additive from Dow Coating Solutions, and 0.73% BYK 346 flow and leveling additive from BYK USA, Wallingford, Conn.

In example 4, the coating solution was developed to 25% volume solids with water and added to the well using a disposable syringe. The well was immediately scraped with the edge of a grind gage scraper from Precision Gage and Tool, 375 Gargrave Road, Dayton, Ohio 45449, to uniform the surface and the time of scrape down was noted. A rim probe of dimensions OD 24.99 mm, ID 23.49 mm having an area of the bottom face of 57.1141 mm$^2$ was lowered to a 0.100 mm gap, and then the dynamic mechanical analyzer (MCR 301 available from Anton Paar Ashland Va.) was run at 0.1% strain and 10 s$^{-1}$ frequency. Changes in viscoelastic properties, complex viscosity (eta*), storage modulus (G'), and loss modulus (G") with time are illustrated in FIG. 7.

Due to the sensitivity of the rheometer and the advantageous configuration of the invention, small torques are easily sensed, even during the early stages of the drying. Further, it is advantageous to be able to monitor the sample at extremely low strain rates and low frequency as this minimizes changing the internal structure of the sample and more realistically mimics true sample drying without disturbance of the film by the probe. This is in contrast to the T-bar probe described in U.S. Pat. Nos. 7,185,530 B2, and 7,472,584 B2 by Seo et al. which apparently requires a strain of 100% and a frequency of 25 rad/sec.

Figure 8:
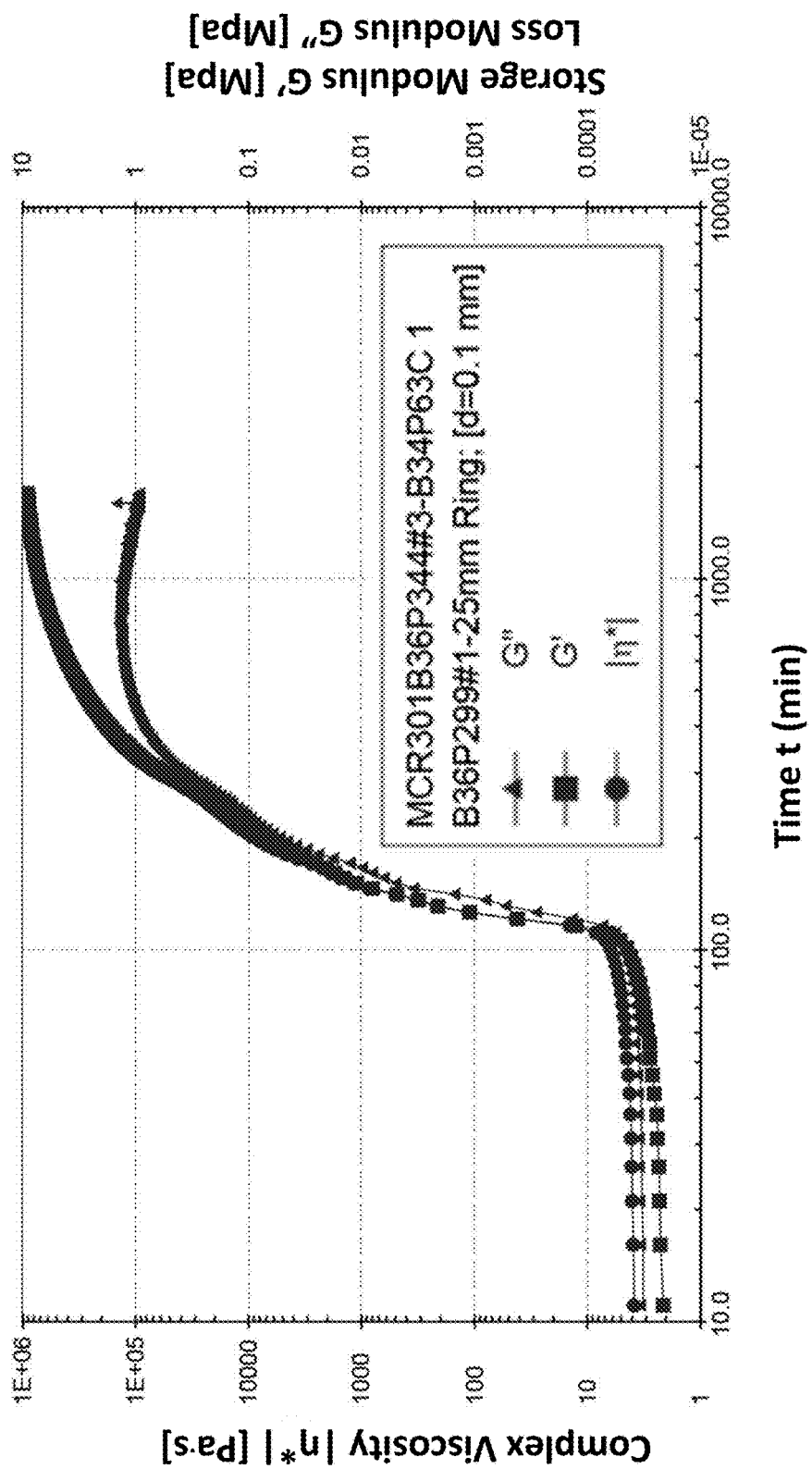
FIG. 8. Illustrates a graphic representation of the viscoelastic properties, (complex viscosity, loss and storage moduli) of an aqueous acrylic lacquer that utilizes an alkyl acetate (Exxate 700) as coalescing additive in a 150 micron well as a function of time.

Further, in contrast to the T-bar probe described by Seo, there is no need to remove the probe before complete consolidation of the film due to fear of damage to the probe. As illustrated in FIG. 8, the viscoelastic properties of the film are followed completely to full film consolidation. e.g. to an approximate constant storage modulus and complex viscosity. The consolidated film may then be evaluated by dynamic mechanical analysis (DTMA, Frequency sweep, Amplitude sweep and others) insitu without further preparation.

Further, the probe is easily cleaned and prepared for the next run by sonication in a cleaning solution consisting of approximately 35% N-Methyl-2-Pyrrolidone, approximately 35% ethylene glycol monobutyl ether, approximately 15% xylene, and approximately 15% Methyl ethyl ketone. Water may be added to the solution. The cleaning solution is effective at cleaning the probe even if the liquid is a thermoset composition.

What is claimed is:

1. A device for examining the rheological properties of a film, the device comprising:
   (a) a substrate configured to support a liquid film,
   (b) a reinforced rim probe configured to sense a viscoelastic response in the liquid film as the liquid film solidifies and viscoelastic properties of the solidified liquid film,
      wherein the substrate and the rim probe are attached to a dynamic oscillatory rheometer,
      wherein the rim probe is brought into contact or immersed in the liquid film, and
      wherein the rim probe further comprises a shank, wherein the shank is positioned at the center of the rim probe and perpendicular to a plane defined by a rim of the rim probe and wherein the rim probe is attached to the rheometer via the shank.

2. The device of claim 1, wherein the rim probe is a spoke reinforced rim probe further comprising at least one spoke.

3. The device of claim 2, wherein a clearance under the at least one spoke separates the at least one spoke from the liquid film by a distance ranging from 0.1 mm to 5 mm.

4. The device of claim 1, wherein the rheometer is configured to effect relative movement between the rim probe and the substrate so that the rim probe moves relative to the liquid film and senses the viscoelastic response to movement of the rim probe contacting or immersed in the liquid.

5. The device of claim 1, wherein the rim probe detects the viscoelastic response of the liquid film over time and provides the viscoelastic response to a sensor that measures a torque and a phase angle between an input signal from the sensor and an output signal from the rim probe as the liquid film solidifies.

6. The device of claim 5, wherein the torque and the phase angle are used to determine the complex viscosity (Eta*), loss modulus (G"), and the storage modulus (G').

7. The device of claim 1, wherein the substrate is a well or a flat plate.

8. The device of claim 7, wherein the substrate is a well having a depth from 5 microns to 10000 microns.

9. The device of claim 1, wherein a transducer examines the viscoelastic response of the movement of the probe and a motor moves the substrate relative to the rim probe.

10. The device of claim 1, wherein the rim probe penetrates the liquid film without contacting the substrate.

11. The device of claim 10, wherein the gap between the substrate and a bottom of the rim probe is from 10 microns to 200 microns.

12. The device of claim 1, wherein a rim of the rim probe has an outer diameter that ranges from 2 mm to 80 mm and/or an inner diameter that ranges from 0.5 mm to 78.5 mm.

13. The device of claim 1, wherein a rim of the rim probe has an inner diameter that ranges from 6.5 mm to 38.5 mm.

14. The device of claim 1, wherein a bottom face of a rim of the rim probe has a surface area that ranges from 5 mm$^2$ to 200 mm$^2$.

15. The device of claim 1, wherein a rim of the rim probe has a circular cross-section, a rectangular cross-section, a rounded cross-section, or a v-shaped cross-section.

16. The device of claim 1, wherein the rim probe is made of one carbon steel, stainless steel, or tungsten carbide.

17. The device of claim 1, wherein the rim probe remains in contact with the film after solidification of the film to perform dynamic mechanical thermal analysis of the solidified liquid film.

18. The device of claim 1, wherein the rim probe detects the viscoelastic response of the solidified liquid film as a function of temperature and provides the viscoelastic response to a sensor that measures a torque and a phase angle between a sinusoidal input signal from the sensor and an output signal from the rim probe as the temperature changes.

19. The device of claim 1, wherein the rim probe remains in contact with the film after solidification of the film to perform an amplitude sweep or a frequency sweep of the solidified liquid film.

20. The device of claim 1, wherein the rim probe detects the viscoelastic response of the solidified liquid film as a function of strain amplitude and/or frequency and provides the viscoelastic response to a sensor that measures a torque and a phase angle between a sinusoidal input signal from the sensor and an output signal from the rim probe as the strain amplitude and/or the frequency is changed.

* * * * *